US00RE34076E

United States Patent [19]

Takeshita et al.

[11] E Patent Number: Re. 34,076

[45] Reissued Date of Patent: Sep. 22, 1992

[54] METHOD FOR PRODUCING HYDROXY-CONTAINING ALKYLATED AROMATIC COMPOUNDS

[75] Inventors: Akira Takeshita; Shinzaburo Masaki; Takeo Fujii, all of Osaka; Tooru Tokumaru; Akira Murakami, both of Ooita, all of Japan

[73] Assignee: Sumitomo Chemical Company Limited, Osaka, Japan

[21] Appl. No.: 730,116

[22] Filed: Jul. 15, 1991

Related U.S. Patent Documents

Reissue of:

[64] Patent No.: 4,912,264
Issued: Mar. 27, 1990
Appl. No.: 59,119
Filed: Jun. 3, 1987

[30] Foreign Application Priority Data

| | | | |
|---|---|---|---|
| Jun. 10, 1986 | [JP] | Japan | 61-133998 |
| Jun. 10, 1986 | [JP] | Japan | 61-133999 |
| Oct. 24, 1986 | [JP] | Japan | 61-254340 |
| Oct. 24, 1986 | [JP] | Japan | 61-254341 |
| Oct. 31, 1986 | [JP] | Japan | 61-260989 |
| Oct. 31, 1986 | [JP] | Japan | 61-260990 |

[51] Int. Cl.[5] ..... C07C 37/14

[52] U.S. Cl. ..... 568/790; 568/791; 568/792; 568/794

[58] Field of Search ..... 568/790, 794, 791, 789, 568/792, 784

[56] References Cited

U.S. PATENT DOCUMENTS

| | | | |
|---|---|---|---|
| 2,572,019 | 10/1951 | Fawcett et al. | 568/789 |
| 2,825,704 | 3/1958 | Arnold et al. | 568/789 |
| 2,831,898 | 4/1958 | Ecke et al. | 568/794 |
| 3,201,486 | 8/1965 | Bielawski | 568/790 |
| 4,568,778 | 2/1986 | Imanari et al. | 568/789 |
| 4,912,264 | 3/1990 | Takeshita et al. | 568/790 |

FOREIGN PATENT DOCUMENTS

| | | | |
|---|---|---|---|
| 155332 | 9/1984 | Japan | 568/790 |

OTHER PUBLICATIONS

Patent Abstracts of Japan, vol. 9, No. 1 (C-259)[1924], Jan. 5, 1985.

Patent Abstracts of Japan, vol. 11, No. 60 (C-405)[2507], Feb. 24, 1987

Chemical Abstracts 107:216858m, 1987.

*Primary Examiner*—Werren B. Lone

*Attorney, Agent, or Firm*—Wenderoth, Lind & Ponack

[57] ABSTRACT

Process for producing hydroxy-containing alkylated aromatic compounds by the liquid phase reaction of an aromatic compound having at least one hydroxyl group with an alkylating agent in the presence of a heteropoly acid and water.

12 Claims, No Drawings

METHOD FOR PRODUCING HYDROXY-CONTAINING ALKYLATED AROMATIC COMPOUNDS

Matter enclosed in heavy brackets [ ] appears in the original patent but forms no part of this reissue specification; matter printed in italics indicates the additions made by reissue.

The present invention relates to a novel method for producing a hydroxy-containing alkylated aromatic compound by reacting an aromatic compound having at least one hydroxyl group with an alkylating agent in a liquid phase.

Hydroxy-containing alkylated aromatic compounds, particularly alkylphenolic compounds obtained by the reaction of a phenolic compound with an alkylating agent, particularly isobutene or an isobutene-containing gas, are finding wide applications, for example, as antioxidants, stabilizers, intermediates for agricultural chemicals and dyestuffs, materials for resins and industrial chemicals.

Particularly, 2,6-di-tert-butyl-4-methylphenol obtained by reacting p-cresol or a cresol mixture containing p-cresol with isobutene or an isobutene-containing gas in the presence of a heteropoly acid, is typical of the alkylphenolic compounds which are an object of the present invention.

The commonly well-known method to produce alkylphenolic compounds, particularly tert-alkylphenolic compounds, by the alkylation of a phenolic compound with a branched olefin, is one in which the reaction is carried out in the presence of an acid catalyst. For the catalyst in this reaction, it is well known to use sulfuric acid [Industrial and Engineering Chemistry, Vol. 35, pp. 264–272 (1943)], aluminum chloride [Journal of American Chemical Society, Vol. 67, pp. 303–307 (1945)], metalloraryl oxide (U.S. Pat. No. [2,821,898] *2,831,898*), toleunesulfonic acid and toluenesulfonic acid type cation-exchange resin (Japanese Patent Publication No. 18182/1962), cresolsulfonic acid (U.S. Pat. No. 2,733,274), etc.

In practice, however, a phenolic compound is reacted with not isobutene, but a gas containing isobutene, butene-1, butene-2, etc. which is cheaply and easily available in industry, and therefore a method of using the foregoing catalysts has a defect that secalkylphenolic compounds, etc. are produced as by-products in large amounts. It is therefore recommended to use high-purity hydrocarbons as a material.

This method is however industrially disadvantageous because isobutene needs to be previously separated from an isobutene-containing mixture and purified, for example, like more volatile components produced by cracking of petroleum products.

A method of reacting a phenolic compound with an isobutene-containing mixture has been thought to be industrially and economically advantageous to produce tert-alkylphenolic compounds, and has extensively been studied. It is however very difficult to selectively react isobutene in the mixture, i.e. an isobutene-containing mixed gas, so that substantial research for high-selectivity catalysts has been conducted and various kinds of catalyst have been proposed.

Any of these conventionally well-known methods had a defect that increasing the selectivity causes a reduction in the conversion and also a reduction in the absorption rate of isobutene. When increasing the conversion is tried, the utility rate of isobutene increases, but the amounts of sec-alkylphenolic compounds, isobutene polymers and polymers of other olefin gases increase. As a result, for obtaining the desired product become markedly complicated, and besides special treatment of the formed waste liquor becomes necessary.

Also, the exhaust gas cannot be used as it is as fuels because it contains the foregoing polymers in large amounts so that purification and separation operations are necessary. In this respect, said processes may be said to be unsuitable for industrialization.

When the conventionally well-known catalysts such a sulfuric acid, toluenesulfonic acid, etc. are used, sulfonated products and neutral esters (butyl sulfate, etc.) are formed. As is well known, these esters, etc. will remain in the reaction product even by neutralization and washing, and act as a dealkylation catalyst when heated to a high temperature on distillation to fail to produce high-quality alkylphenolic compounds in high yields.

For this reason, a method has so far been employed in which the reaction product is neutralized with an aqueous alkali solution at high temperature and high pressure to decompose the esters [Industrial and Engineering Chemistry, Vol. 35, pp. 265–272 (1943)].

Also, there were many other problems. For example, since these catalysts have a violent corrosive action, equipment of high-grade materials is necessary to use the catalysts in industry.

In view of this present situation like this, the present inventors extensively studied alkylation with an aromatic compound having at least one hydroxyl group and an alkylating agent as starting materials which is capable of producing the desired product in high selectivity, in high yields and with ease by economical and simple operations. As a result, the present inventors found that the desired product is obtained high selectivity and in high yields by carrying out said alkylation in a liquid phase using a heteropoly acid as a catalyst.

Particularly, according to the method of the present invention, it was found that, in the reaction of a phenolic compound with a gas containing isobutene, butene-1, butene-2, etc., there are obtained remarkable effects to inhibit the side reactions of butene-1, butene-2, etc. and prevent the polymerization of isobutene, etc.; the desired alkylphenolic compounds can be produced in extremely high purity and high yield and with ease; and further the heteropoly acid can easily be recovered after reaction, can be re-used in the subsequent reaction and is very low in the corrosive action on equipments so that it is very useful industrially. The present inventors thus completed the present invention.

The foregoing objects of the present invention are attained by the method of the present invention, i.e. by reacting an aromatic compound having at least one hydroxyl group with an alkylating agent in a liquid phase and in the presence of a heteropoly acid.

The method of the present invention will be illustrated in more detail hereinafter.

Starting Material

For the aromatic compound having at least one hydroxyl group used in the present invention the following compounds can be given: Monohydric phenols such as phenol, o-, m- or p-cresol and mixtures thereof, o-, m-or p-ethylphenol, o-, m- or p-isopropylphenol, o-, m- or p-tert-butylphenol, o-, m- or p-sec-butylphenol, 4-tert-butyl-6-methylphenol, 2,4-dimethylphenol, 2-4-ethylphenol, 2,4-diisopropylphenol, 4-methyl-6-isopropylphenol, 2,6-di-tert-butylphenol, 2-tert-butyl-4-methylphenol, 3-methyl-6-tert-butylphenol, 2-chloro-4-methylphenol, p-chlorophenol, p-bromophenol, 2,4-dichlorophenol, 2,4-dibromophenol, 2-methyl-4-chlorophenol, 2-methyl-4-bromophenol, 2,4-dichloro-3-methylphenol, 3-methyl-6-cyclohexylphenol, 3-methyl-4-cyclohexylphenol, etc.; polyhydric phenols such as resorcinol, hydroquinone, catechol, 2-methylresorcinol, 2-chlororesorcinol, 2-carboxyresorcinol, 2-chlorohydroquinone, 4-tert-butylresorcinol, phloroglucinol, etc.; and naphthols such as 1-naphthol, 2-naphthol, 2-hydroxy-3-carboxynaphthalene, 1-hydroxy-5-methylnaphthalene, 2-hydroxy-5-methylnaphthalene, 2-hydroxy-8-isopropylnaphthalene, 2-hydroxy-5-isopropylnaphthalene, etc.

Of these compounds, cresols (including mixed cresols), resorcinol, etc. are preferably used.

The alkylating agent used in the present invention includes unsaturated hydrocarbons having at least one double bond, aliphatic alcohols, etc.

The unsaturated hydrocarbon containing a double bond includes *isobutene*, a compound represented by the general formula (I), $$R_1—CH=CH_2 \quad (I)$$

wherein $R_1$ represents a hydrogen atom or a straight or branched hydrocarbon residue having from 1 to 10 carbon atoms, a compound represented by the general formula (II), $$R_2—CH=CH—CH_3 \quad (II)$$

wherein $R_2$ represents a straight or branched hydrocarbon residue having from 1 to 9 carbon atoms, and a cyclic unsaturated hydrocarbon having up to 10 carbon atoms.

Specific examples of these hydrocarbons include ethyelene, propylene, 1-butene, 2-butene, isobutene, 1-pentene, 2-pentene, isopentene, 1-hexene, 2-hexene, 1-heptene, 2-heptene, 1-octene, 2-octene, 1-nonene, 2-nonene, 1-decene, 1-dodecene, 2-dodecene, cyclopropene, cyclobutene, cyclopentene, cyclohexene, cyclooctene, etc.

The aliphatic alcohol includes methanol, ethanol, isopropanol tert-butanol, sec-butanol, pentanol, hexanol, benzyl alcohol, cyclohexanol, etc.

These alkylating agents may also be used in a mixture of two or more of them. As examples of the mixture, an isobutene-containing gas containing 1-butene, 2-butene, etc. in addition to isobutene (hereinafter referred to as LBB gas) is preferably used.

In carrying out the present invention, the alkylating agent may be used in any proportion, but its amount is generally from 0.1 to 30 times, preferably from 1 to 20 times, more preferably from 1 to 5 times by molar amount, based on the aromatic compound having at least one hydroxyl group.

In polyalkylation wherein two or more alkyl groups are introduced into an aromatic ring, the amount of the alkylating agent is generally from 2 to 50 times, preferably from 2 to 20 times, more preferably from 2 to 5 times, by molar amount.

<Catalyst>

In the method of the present invention, it is essential to employ a heteropoly acid as a catalyst. The heteropoly acid referred to herein is an acid formed by two or more metals among polyacids formed by bonding with an inorganic acid. Generally, the heteropoly acid is the generic name of compounds comprising one kind of metal (or hetero-atom) located at the center and another kind of metal (polyatom) coordinated to the former metal through oxygen, etc. The hetero-atom includes boron aluminum, silicon, phosphorus, titanium, germanium, arsenic, zirconium, tin, tellurium, etc., and the polyatom includes molybdenum, tungsten, vanadium, niobium, etc.

Specifically, there are given phosphomolybdic acid, silicomolybdic acid, arsenomolybdic acid, telluromolybdic acid, aluminomolybdic acid, silicotungstic acid, phosphotungstic acid, borotungstic acid, titanotungstic acid, stannotungstic acid, etc. Of these compounds, phosphomolybdic acid, silicomolyhdic acid, phosphotungstic acid, silicotungstic acid, etc. are particularly preferably used, and silicotungstic acid is most preferably used.

These heteropoly acids are generally used in the form of a hydrate.

The amount of these catalysts used varies with reaction forms and other conditions, but it is generally from 0.00001 to 0.3 times by weight, preferably from 0.0001 to 0.1 times by weight, more preferably from 0.0002 to 0.03 time by weight based on the aromatic compound.

The amount of the heteropoly acid used in the method of the present invention need not always be limited to a low level, considering that the acid is recovered after reaction, for example, as an aqueous solution and re-used. It is rather preferred to use the acid in relatively large amounts so that the reaction proceeds stably, and obtain advantageous results by the recovery and re-use of the acid.

<Reaction conditions>

The reaction of the present invention is characterized in that is carried out in a liquid phase and in the presence of the foregoing heteropoly acid, which is very advantageous in terms of operation, economy and equipment to carry it out in a commercial scale.

In the method of the present invention, the reaction temperature is generally from 20° to 200° C., preferably from 30° to 150° C., more preferably from 40° to 90° C. Too low temperatures retard the reaction rate, while too high temperatures show a tendency to increase the amount of by-products.

In the method of the present invention, the reaction time is not critical and generally, a period of from about 0.5 to about 50 hours is sufficient.

In the method of the present invention, the manner of introducing the alkylating agent into the reaction system is not critical and when for example an LBB gas is used, the agent may be introduced into the reaction system in the form of a gas or liquid.

Depending upon the reaction conditions, the heteropoly acid, a catalyst may be used as undissolved, i.e. in the state of heterogeneous system. In this case, water, acetone, etc., may coexist in the system as a diluent or dissolving agent. The amount of such water, acetone, etc. is generally from 0.1 to 20 times by weight, preferably from 0.5 to 5 times by weight based on the heteropoly acid.

In carrying out the method of the present invention, the selectivity and yield of the desired alkylphenolic compounds, particularly tert-alkylphenolic compounds can be increased by causing a certain amount of water to exist in the reaction system.

Thus, we have found that the above object can be attained by causing water to exist in the reaction system, the amount of water being in a range of from 0.0001 to 0.10 part by weight, preferably from 0.001 to 0.05 part by weight, more preferably from 0.002 to 0.03 part by weight based on the phenolic compound, a starting material.

Hereupon in determining the amount of water to exist in the reaction system, the water of crystallization of the heteropoly acid used as a catalyst is also taken into account.

Consequently, if the water content of the reaction system is regulated within the above range by increasing the amount of water to exist when the amount of the heteropoly acid used is large, and vice versa the reaction proceeds more smoothly to make it possible to attain high selectivity and high yield.

When the amount of water present in the system is beyond the above range, the reaction of a phenolic compound with isobutene slows down, and large amounts of the unreacted phenolic compound and intermediate products are left behind. While when the amount of water present in the system is below this range, there was found a tendency that the reaction of a phenolic compound with butene-1, butene-2, etc. contained in an LBB gas proceeds at a rate equal or to or more rapidly than that of a phenolic compound with isobutene to produce sec-alkylphenolic compounds, which are an unpreferred byproduct, in large amounts.

This is completely beyond expectation from the common sense in the art that, in a system wherein reaction is carried out using a solid acid catalyst, coexistence of water causes a reduction in the acid strength accompanied by a reduction in the catalytic activity.

When a large amount of the phenolic compound, a starting material, is left unreacted, troublesome operations are necessary to recover the phenolic compound, or when undesirable by-products are contained in large amounts in spite of use of an LBB gas which is easily and cheaply available in industry, troublesome and difficult purification operations are necessary. It is therefore very important to determine the reaction conditions so as to avoid the above troublesome operations, and for this purpose, it becomes essential to carry out the reaction within the range of water content found by the present invention.

Any of pure water, industrial water, recovered water, steam, etc. may be used as water to exist in the reaction system.

Incorporation of water in the reaction system is attained by feeding the phenolic compound, a starting material, and the heteropoly acid to the system and then introducing a prescribed amount of water into the system. As another method, a method may also be used in which the water content of the phenolic compound is previously controlled so that, when the compound and the heteropoly acid have been fed, the water content of the system is in the pre-determined range.

Alternatively, a method may also be used in which the concentration of an aqueous heteropoly acid solution is previously controlled so that, when the solution and the phenolic compound, a starting material, have been fed, the water content of the system is in the predetermined range. Any of the above methods may be used.

It is also a remarkable feature of the present invention that when the heteropoly acid is used as catalyst according to the method of the present invention, high-boiling products such as butene dimers, etc. are hardly produced in the exhaust gas. That is, in producing alkylphenolic compounds from isobutene or an LBB gas, using sulfuric acid, etc. as catalyst increases the butene dimer content of the exhaust gas, so that the gas cannot be used as it is as fuels, city gases, etc. Consequently, operation for removing these high-boiling products from the exhaust gas becomes necessary, which is disadvantageous industrially. On the other hand, the method of the present invention produces few high-boiling products from butenes, so that it has an advantage that high-quality liquefied petroleum gas can easily be recovered by merely compressing the exhaust gas.

As a matter of course, the reaction form of the method of the present invention is not limited to those described in the examples but a batchwise or continuous form carried out at atmospheric pressure or under pressure may be used.

The reaction may be carried out with or without a solvent.

The solvent usable in the reaction includes aromatic hydrocarbons such as benzene, toluene, xylene, ethylbenzene, ethyltoluene, cumene, nitrobenzene, chlorobenzene, etc., and ethers such as isopropyl ether, etc. The amount of the solvent used gives no large influence, and it is preferably from 0.5 to 50 times by weight, more preferably from 1 to 20 times by weight based on the aromatic compound having at least one hydroxyl group.

<Treatment after reaction>

As described above, when sulfuric acid or toluenesulfonic acid is used as catalyst, neutral esters (butyl sulfate, etc.) are formed, so that neutralization at high temperature and under pressure is essential. In carrying out the present invention, however, it was found that no impurities such as sulfuric esters are formed and neutralization treatment is possible under very mild conditions. That is, complete removal of impurities is possible by merely neutralizing or washing the reaction product with an aqueous alkali solution or warm water.

A temperature at which the neutralization or washing is carried out need not be high unlike the conventional methods, and impurities can sufficiently be removed at a temperature of from 40° to 90° C.

As the amount of the aqueous alkali solution or warm water, an amount enough to make the aqueous layer neutral will suffice and it is generally from 0.1 to 10 times by weight, preferably from 0.2 to 5 times by weight based on the reaction product. When this aqueous alkali solution or warm water is used not at one time, but in several portions, the removal effect becomes even better.

Contact between the aqueous alkali solution or water water and the reaction product is attained by stirring-contact for from 5 minutes to 10 hours, preferably from 10 minutes to 5 hours. The aqueous alkali solution can be prepared, for example, with sodium hydroxide and water.

Contact between the aqueous alkali solution or warm water and the reaction product is attained by stirring-contact for from 5 minutes to 10 hours, preferably from 10 minutes to 5 hours. The aqueous alkali solution can be prepared, for example, with sodium hydroxide and water.

In producing alkylphenolic compounds by the reaction of a phenolic compound with isobutene or an isobutene-containing gas, the amount of the heteropoly acid which precipitates in the system increases with the progress of the reaction, and by the time the reaction comes to an end, most of the heteropoly acid precipitates.

The heteropoly acid, a precipitate, is separated from the reaction solution which may or nay not be cooled. This separation can be attained sufficiently by the usual separation techniques such as filtration, centrifugation, decantation, etc.

In separating the heteropoly acid complete solid-liquid separation is unnecessary, and even heteropoly acid containing the reaction solution in large amounts can sufficiently be re-used. Also, the oily layer may contain the heteropoly acid as a solid, if the amount of the heteropoly acid is of such a degree that there are no adverse effects such as dealkylation at the subsequent distillation step.

Even if neutralization with an aqueous alkali solution is carried out before distillation an extremely a small amount of alkali will suffice.

For separating the heteropoly acid from the reaction mixture after reaction there is another method for treating the reaction mixture with water to dissolve the heteropoly acid in the aqueous layer and separating the oily layer by means such as liquid-liquid separation etc. In this case, any of pure water, industrial water, recovered water, steam, etc. may be used as water for treatment of the reaction mixture.

For extraction-recovering the heteropoly acid catalyst by treatment of the reaction mixture with water, any of a counter-flow or parallel-flow batch process and a counter-flow or parallel-flow continuous process may be used.

For recovering the heteropoly acid and re-using it in the next reaction, it is practically advantageous to adjust the heteropoly acid content of the aqueous layer to 20 wt. % or more, preferably 30 wt. % or more.

Any amount of water may be added to recover the heteropoly acid by the batch process, but it is preferred to resist the concentrations of the aqueous heteropoly acid solution recovered by this process within the above range so that the solution can be re-used in the next reaction. When, however, the volume ratio of oily layer to aqueous layer, because of the heteropoly acid catalyst being small in amount, is too large to separate the aqueous layer from the other one, it is also possible to extraction-recover the heteropoly acid catalyst with an increased amount of water and vaporize water to the foregoing desired concentration of the heteropoly acid.

After completion of the reaction, when precipitated heteropoly acid is present in the system, it is preferred to add a minimal amount of water necessary to dissolve the heteropoly acid.

Water to be added after completion of the reaction may be added at a time or in several portions.

When the heteropoly acid is recovered by the continuous process wherein the reaction mixture is continuously supplied to a mixer-settler containing a prescribed amount of water, continuously mixed and separated into aqueous and oily layers, it is possible to operate the process so that the heteropoly acid concentration of the aqueous layer is in the desired range described above, so that this continuous process is industrially advantageous. This process can be carried out in either single-stage or multi-stage, and the percent recovery of the heteropoly acid can be made 95% or more. Also, it is necessary to continuously supply water to the settler so that the amount of water does not decrease below the prescribed one, because water in the settler decreases in solution in the reaction mixture. The mixer-settler is preferably a vertical-type mixer/settler assembly with the lower part as mixer and the upper part as settler. Even when the mixer and settler are used separately, the object can be attained by circulating the aqueous layer from the settler to the mixer.

Further, various kinds of extractor commonly used can be used for the purpose of the present invention, and as need arises, it is also possible to pack a net made of glass fibers, polymer fibers, etc., for example. "Coalescer" (a trade name of Nihon Mesh K.K.,), between the mixer and settler in order to improve the separation of the oily and aqueous layers.

In this case, a temperature at which separation of the oily and aqueous layers is carried out should be higher than that below which the desired alkylphenolic compounds crystallize. Industrially, the separation is carried out at a temperature at which the reaction has come to an end or at one somewhat lower than that.

The heteropoly acid separated and recovered in this way is re-used in the next reaction, and in this case, it is preferred to cause a definite amount of water to exist in the reaction system, as described above.

<Treatment of reaction solution after separation of heteropoly acid>

The reaction solution after removal of the heteropoly acid from the system is washed or neutralized with a small amount of water or aqueous alkali and in the case of reaction carried out with a solvent, the desired alkylphenolic compounds can be obtained by separation removal of the solvent by the usual methods.

If necessary, the product can be purified by distillation, extraction, recrystallization, etc.

A further detailed explanation will be given below, of a method for producing typical alkylphenolic compounds of the present invention by the reaction of a cresol with isobutene or an isobutene-containing gas.

After separating the heteropoly acid from the reaction mixture by the method described above, high-purity 2,6-di-tert-butyl-4-methylphenol can be obtained from the oily layer easily and in high yields (that is, without dealkylation) under a mild industrial distillation condition.

For example, after dehydration and removal of low-boiling components by heating the oily layer to a temperature of from 100° to 160° C. at atmospheric pressure the monobutyl derivative is removed by distillation at from 120° to 160° C. under a reduced pressure of from 20 to 100 Torr, and then desired 2,6di-tert-butyl-4-methylphenol is obtained by distillation at from 140° to 200° C. under a reduced pressure of from 10 to 70 Torr.

This distillation (rectification) can be carried out by a continuous or batch process, its condition not being limited to only those described above.

2,6-Di-tert-butyl-4-methylphenol contained in the oily layer is recovered almost quantitatively without being decomposed, for example, by debutylation, and yet the monobutyl derivative, a low-boiling component, can be recovered almost quantitatively. These compounds are used in cycle for butylation.

When a cresol mixture containing p-cresol is used as a starting material, a high-boiling fraction left behind after removal of 2,6-di-tert-butyl-4-methylphenol by distillation contains 4,6-di-tert-butyl-3-methylphenol as a main component, and this component is also recovered almost quantitatively without being decomposed for example, by debutylation.

The heteropoly acid used in the method of the present invention has a high activity and a high selectivity, so that the desired alkylated products, particularly hydroxy-containing alkylated aromatic compounds can be obtained industrially advantageously and in high yields.

Particularly the heteropoly acid has advantages that there is no formation of impurities such as sulfonated products and yet after-treatment can easily be conducted under very mild conditions.

Further, the heteropoly acid is very useful from the industrial standpoint in that it is low in corrosive action on equipment so that even equipment of cheap material can be used in a reaction at high temperature.

The present invention will be illustrated in more detail with reference to the following examples, but it is not limited thereto as long as within the spirit and scope of the following claims.

Parts and percents (%) in the examples are by weight.

EXAMPLE 1

100 Parts of a cresol mixture (p-cresol, 70%; m-cresol, 30%) and 0.04 part of phosphotungstic acid were added to a flask, and 288 parts of an LBB gas (isobutene content, 45%) was bubbled into the mixture over 8 hours with stirring while maintaining the temperature at from 60° to 65° C.

The weight of the reaction mixture was 195.1 parts.

On washing the reaction product with water and aqueous alkali, 186.5 parts of an oily product was obtained. The composition of this oily product was analyzed by gas chromatography to obtain the following results:

| | |
|---|---|
| Unreacted cresol | 1.5% |
| 2-Tert-butyl-4-methylphenol | 19.5% |
| 6-Tert-butyl-3-methylphenol | 5.6% |
| 2,6-Di-tert-butyl-4-methylphenol | 44.2% |
| 4,6-Di-tert-butyl-3-methylphenol | 22.5% |
| Others | 6.7% |

EXAMPLE 2

100 Parts of a cresol mixture (p-cresol, 70%; m-cresol, 30%) and 0.15 part of silicotungstic acid were added to a flask, and 288 parts of a LBB gas (isobutene content, 45%) was bubbled into the mixture over 10 hours with stirring while maintaining the temperature at from 45° to 55° C.

The weight of the reaction mixture was 210.3 parts.

On washing the reaction product with water and aqueous alkali, 192.5 parts of an oily product was obtained. The composition of this oily product was analyzed by gas chromatography to obtain the following result:

| | |
|---|---|
| Unreacted cresol | 0.9% |
| 2-Tert-butyl-4-methylphenol | 19.1% |
| 6-Tert-butyl-3-methylphenol | 3.6% |
| 2,6-Di-tert-butyl-4-methylphenol | 42.8% |
| 4,6-Di-tert-butyl-3-methylphenol | 24.3% |
| Others | 9.3% |

EXAMPLE 3

100 Part of p-cresol and 0.9 part of phosphomolybdic acid were added to a flask, and 100 parts of an isobutene gas was bubbled into the mixture over 5 hours with stirring while maintaining the temperature at from 55° to 65° C.

The weight of the reaction mixture was 206.7 parts.

On washing the reaction product with water and aqueous alkali, 198.3 parts of an oily product was obtained. The composition of this oily product was analyzed by gas chromatographic to obtain the following result:

| | |
|---|---|
| Unreacted p-cresol | 1.0% |
| 2-Tert-butyl-4-methylphenol | 7.1% |
| 2,6-Di-tert-butyl-4-methylphenol | 85.4% |
| Others | 6.5% |

The content of isobutene dimer and isobutene trimer of the unreacted gas was 1.2%.

EXAMPLE 4

100 Parts of a cresol mixture (p-cresol, 70%; m-cresol, 30%) and 0.02part of silicotungstic acid were added to a flask, and 100 parts of an isobutene gas was bubbled into the mixture over 6 hours with stirring while maintaining the temperature at from 70° to 75° C.

On washing the reaction product with water and aqueous alkali, 193.5 parts of an oily product was obtained. The composition of this oily product was analyzed by gas chromatography to obtain the following result:

| | |
|---|---|
| Unreacted cresol | 0.9% |
| 2-Tert-butyl-4-methylphenol | 6.0% |
| 6-Tert-butyl-3-methylphenol | 1.5% |
| 2,6-Di-tert-butyl-4-methylphenol | 60.1% |
| 4,6-Di-tert-butyl-3-methylphenol | 26.4% |
| Others | 5.1% |

EXAMPLE 5

To 94.1 parts of phenol was added 0.06 part of silicotungstic acid, and 118 parts of an isobutene gas was bubbled into the mixture over 4 hours with stirring while maintaining the temperature at from 50° to 60° C.

The weight of the reaction mixture was 200.7 parts.

On washing the reaction product with water and aqueous alkali, 190.1 parts of an oily product was obtained.

The composition of this oily product was analyzed by gas chromatography to obtain the following result:

| | |
|---|---|
| Unreacted phenol | 1.5% |
| 2-Tert-butylphenol | 15.4% |
| 4-Tert-butylphenol | 9.6% |
| 2,6-Di-tert-butylphenol | 15.5% |
| 2,4-Di-tert-butylphenol | 37.5% |
| 2,4,6-Tri-tert-butylphenol | 14.7% |
| Others | 5.8% |

EXAMPLE 6

To 54.8 parts of o-cresol was added 1.0 part of phosphotungstic acid, and 17 parts of an isobutene was bubbled into the mixture over 5 hours with stirring while maintaining the temperature at from 50° to 55° C.

The weight of the reaction mixture was 104.5 parts.

By gas-chromatographic analysis, the following result was obtained:

| | |
|---|---|
| Unreacted o-cresol | 1.5% |
| 6-Tert-butyl-2-methylphenol | 6.5% |
| 4-Tert-butyl-2-methylphenol | 10.1% |
| 4,6-Di-tert-butyl-2-methylphenol | 76.7% |
| Others | 5.2% |

The content of isobutene dimer and isobutene trimer of the unreacted gas was 1.0%.

EXAMPLE 7

40 Parts of resorcinol, 200 ml of toluene (solvent) and 1.2 parts of silicotungstic acid were added to a flask, and an isobutene gas was bubbled into the mixture with stirring while maintaining the temperature at from 50° to 60° C.

After reaction the precipitated catalyst was filtered off and washed with 40 ml of water. The washing was concentrated to 200 ml under reduced pressure and after adding 20 ml of water, cooled with ice. The precipitated crystals were recovered by filtration and dried under reduced pressure to obtain 79.5 parts of a solid. By gas-chromatographic analysis, it was found that 98.5%-purity 4,6-di-tert-butylresorcinol was obtained.

EXAMPLE 8

To 54.1 parts of m-cresol was added 12 parts of phosphomolybdic acid, and 45.2 parts of cyclohexene was added dropwise to the mixture over 3 hours with stirring while maintaining the temperature at from 90° to 95° C.

The weight of the reaction mixture was 98 parts.

By gas-chromatographic analysis, the following result was obtained:

| | |
|---|---|
| 6-Cyclohexyl-3-methylphenol | 10.2% |
| 4-Cyclohexyl-3-methylphenol | 20.5% |
| 4,6-Dicyclohexyl-3-methylphenol | 1.2% |

EXAMPLE 9

94 Parts of phenol and 0.9 part of silicotungstic acid were added to a flask, and 50 parts of ethanol was added dropwise over 2 hours with stirring while maintaining the temperature at from 90° 100° C., after which the reaction solution was kept at from 100° to 120° C. for 5 hours.

The conversion of phenol was 20%.

The composition of the reaction product obtained by removing the unreacted phenol and ethanol from the reaction mixture was as follows:

| | |
|---|---|
| Phenethol | 13% |
| o-Ethylphenol | 42% |
| m-Ethylphenol | 3% |
| p-Ethylphenol | 37% |
| 2,4-Diethylphenol | 5% |

EXAMPLES 10 to 16

Using the same reactor and procedure as in Example 1, reaction was carried out in completely the same manner as in Example 1 except that the kinds of the aromatic compound and alkylating agent and other reaction conditions were varied. The results obtained are shown in Table 1.

TABLE 1

| Example | Aromatic compound | Amount used (part) | Heteropoly acid | Amount used (part) | Solvent and others | Amount used (part) |
|---|---|---|---|---|---|---|
| 10 | m-Cresol | 49.6 | Phosphomolybdic acid | 0.04 | | |
| 11 | p-Cresol | 43.8 | Phosphotungstic acid | 0.8 | | |
| 12 | 2-Tert-butyl-4-methylphenol | 146.6 | Silicotungstic acid | 3.0 | Water | 1.5 |
| 13 | Phenol | 94.1 | Silicotungstic acid | 1.9 | Water | 1.0 |
| 14 | 2-Naphthol | 30 | Silicotungstic acid | 0.2 | Toluene | 300 |
| 15 | 2-Ethylphenol | 50 | Silicotungstic acid | 0.5 | Water | 0.5 |
| 16 | Phenol | 20 | Phosphotungstic acid | 0.4 | Toluene | 200 |

| Example | Temperature (°C.) | Alkylating agent | Amount used (part) | Time (hr) | Conversion (%) | Selectivity of monoalkyl derivative (%) | Selectivity of dialkyl derivative (%) |
|---|---|---|---|---|---|---|---|
| 10 | 65–70 | 1-Butene | 26 | 7 | 20 | 65.5 | 24.0 |
| 11 | 60–65 | Tert-butanol | 75 | 10 | 12 | 75 | 8.3 |
| 12 | 45–50 | Isobutene | 62 | 5 | 56 | 14 | 81 |
| 13 | 80–85 | Propylene | 80 | 7 | 60 | 52 | 30 |
| 14 | 100–110 | Isobutene | 25 | 7 | 53 | 25 | 63 |
| 15 | 80–85 | 1-Hexene | 52 | 5 | 25 | 71 | 13 |
| 16 | 130–140 | 1-Dodecene | 55 | 15 | 15 | 83 | 7 |

EXAMPLE 17

100 Parts of a cresol mixture (p-cresol, 70%; m-cresol, 30%) and 1 part of silicotungstic acid were added to a flask, and water was added so that the water content of the mass in the flask was 0.025 time by weight based on the cresol mixture.

Thereafter, 288 parts of an LBB gas (isobutent content, 45%) was bubbled into the mass over 5 hours with stirring while maintaining the temperature at from 45° to 55° C.

The weight of the reaction mixture was 206.3 parts.

On washing the reaction product with water and aqueous alkali, 191.5 parts of an oily product was obtained. The composition of this oily product was analyzed by gas chromatography to obtain the following result:

| | |
|---|---|
| Unreacted cresol | 0.7% |
| 2-Tert-butyl-4-methylphenol | 17.8% |
| 6-Tert-butyl-3-methylphenol | 2.4% |
| 2,6-Di-tert-butyl-4-methylphenol | 48.1% |
| 4,6-Di-tert-butyl-3-methylphenol | 26.4% |
| Others | 4.6% |

EXAMPLE 18

100 Parts of a cresol mixture (p-cresol, 70%; m-cresol, 30%) and 1 part of phosphotungstic acid were added to a flask, and water was added so that the water content of the mass in the flask was 0.002 time by weight based on the cresol mixture.

Thereafter, 288 parts of a LBB gas (isobutene content, 45%) was bubbled into the mass over 7 hours with stirring while maintaining the temperature at from 55° to 60° C.

The weight of the reaction mixture was 204.1 parts.

On washing the reaction product with water and aqueous alkali, 194.1 parts of an oily product was obtained. The composition of this oily product was analyzed by gas chromatography to obtain the following result:

| | |
|---|---|
| Unreacted cresol | 0.6% |
| 2-Tert-butyl-4-methylphenol | 16.9% |
| 6-Tert-butyl-3-methylphenol | 3.2% |
| 2,6-Di-tert-butyl-4-methylphenol | 48.5% |
| 4,6-Di-tert-butyl-3-methylphenol | 26.6% |
| Others | 5.2% |

EXAMPLE 19

To 100 parts of p-cresol was added 0.8 part of a 50% aqueous silicotungstic acid solution, and 242 parts of an LBB gas (isobutene content, 45%) was bubbled into the mixture over 10 hours with stirring while maintaining the temperature at from 50° to 60° C.

The weight of the reaction mixture was 202.0 parts. The precipitated silicotungstic acid was filtered off by means of a glass filter, and the filtrate was washed with a small amount of water to obtain 200.2 parts of an oily product. The composition of this oily product was analyzed by gas chromatography to obtain the following result:

| | |
|---|---|
| Unreacted p-cresol | 0.7% |
| 2-Tert-butyl-4-methylphenol | 7.3% |
| 2,6-Di-tert-butyl-4-methylphenol | 88.8% |
| Others | 3.2% |

The content of isobutene dimer and isobutene trimer of the unreacted gas was 0.2%.

EXAMPLE 20

To 100 parts of m-cresol was added 1.0 part of a 40% aqueous phosphotungstic acid solution, and 242 parts of an LBB gas (isobutene content, 45%) was bubbled into the mixture over 6 hours with stirring while maintaining the temperature at from 60° to 65° C.

The weight of the reaction mixture was 202.5 parts.

Five parts of water was added to the reaction mixture to dissolve phosphotungstic acid in the aqueous layer, and the oily layer was separated from the aqueous layer. By washing with a small amount of aqueous alkali, 201.8 parts of an oily product was obtained. The composition of this oily product was analyzed by gas chromatography to obtain the following result:

| | |
|---|---|
| Unreacted m-cresol | 0.9% |
| 6-Tert-butyl-3-methylphenol | 7.0% |
| 4,6-Di-tert-butyl-3-methylphenol | 88.6% |
| Others | 3.5% |

EXAMPLE 21

94.1 Parts of phenol and 0.12 part of phosphomolybdic acid were added to a flask, and water was added so that the water content of the mass in the flask was 0.01 time by weight based on phenol. Thereafter, 250 parts of an LBB (isobutene content, 45%) was bubbled into the mass over 3 hours with stirring while maintaining the temperature at from 45° to 55° C. The weight of the reaction mixture was 201.5 parts. On washing the reaction product with water and aqueous alkali, 196.1 parts of oily product was obtained. The composition of this oily product was analyzed by gas chromatography to obtain the following result:

| | |
|---|---|
| Unreacted phenol | 0.9% |
| 2-Tert-butylphenol | 13.1% |
| 4-Tert-butylphenol | 9.6% |
| 2,6-Di-tert-butylphenol | 22.7% |
| 2,4-Di-tert-butylphenol | 34.9% |
| 2,4,6-Tri-tert-butylphenol | 15.8% |
| Others | 3.0% |

EXAMPLES 22 to 27

Reaction was carried out using the same reactor and procedure as in Example 17 except that the kind of a phenolic compound, amount of heteropoly acid, water content of the system and temperature were varied. The results obtained are shown in Table 2.

Symbols in the table mean the following compounds: 4M2B: 2-Tert-butyl-4-methylphenol 3M6B: 6-Tert-butyl-3-methylphenol 4M26B: 2,6-Di-tert-butyl-4-methylphenol 3M46B: 4,6-Di-tert-butyl-3-methylphenol

TABLE 2

| Example | Phenolic compound (part) | Heteropoly acid (part) | Water content of system (time by weight) | Temperature (°C.) | Isobutenes (part) | Time (hr) | Weight of oily product (part) | Composition of oily product | | | | | |
|---|---|---|---|---|---|---|---|---|---|---|---|---|---|
| | | | | | | | | Material | 4M2B | 3M6B | 4M26B | 3M46B | Others |
| 22 | Cresol mixture 100 | Silicotungstic acid 0.1 | 0.003 | 40–50 | LBB gas 250 | 7 | 190.2 | 1.0 | 17.2 | 3.1 | 49.0 | 25.9 | 3.8 |
| 23 | m-Cresol 100 | Silicotungstic acid 0.06 | 0.0067 | 60–70 | Isobutene 108.8 | 12 | 198.9 | 1.0 | — | 8.5 | — | 86.5 | 4.0 |
| 24 | p-Cresol 100 | Silicotungstic acid 0.06 | 0.0020 | 60–70 | Isobutene 108.8 | 7 | 198.0 | 1.1 | 8.7 | — | 87.4 | — | 2.8 |
| 25 | Cresol mixture 100 | Silicotungstic acid 0.06 | 0.0012 | 45–50 | Isobutene 108.8 | 6 | 190.5 | 1.0 | 17.6 | 3.0 | 49.0 | 25.5 | 3.9 |

TABLE 2-continued

| Example | Phenolic compound (part) | Heteropoly acid (part) | Water content of system (time by weight) | Temperature (°C.) | Isobutenes (part) | Time (hr) | Weight of oily product (part) | Composition of oily product | | | | | |
|---|---|---|---|---|---|---|---|---|---|---|---|---|---|
| | | | | | | | | Material | 4M2B | 3M6B | 4M26B | 3M46B | Others |
| 26 | Cresol mixture 100 | Phosphotungstic acid 0.02 | 0.002 | 60–70 | Isobutene 129 | 7 | 189.1 | 1.3 | 18.5 | 2.4 | 46.8 | 27.0 | 4.0 |
| 27 | p-Cresol 100 | Silicotungstic acid 3 | 0.01 | 50–55 | LBB gas 242 | 6 | 201.9 | 0.7 | — | 88.9 | — | 4.0 | |

Remarks
cresol mixture p-cresol 70%, m-cresol 30%
LBB gas: isobutene content 45%

EXAMPLE 28

100 Parts of a cresol mixture (p-cresol, 70%; m-cresol, 30%) and 1 part of silicotungstic acid were added to a flask, and 288 parts of an LBB gas (isobutene content, 45%) was bubbled into the mixture over 5 hours with stirring while maintaining the temperature at from 45° to 55° C.

After completion of the reaction, the precipitated silicotungstic acid was filtered off at a temperature of 45° C. by means of a glass filter (G4). The weight of the recovered silicotungstic acid was 0.99 part, and the water content of the acid was 5.0%.

The content of dissolved silicotungstic acid of the filtrate was 0.002 wt. %.

The filtrate was washed with water and aqueous alkali to obtain 190.8 parts of an oily product. The composition of this oily product was analyzed by gas chromatography to obtain the following result:

| | |
|---|---|
| Unreacted cresol | 1.0% |
| 2-Tert-butyl-4-methylphenol | 17.3% |
| 6-Tert-butyl-3-methylphenol | 2.6% |
| 2,6-Di-tert-butyl-4-methylphenol | 46.0% |
| 4,6-Di-tert-butyl-3-methylphenol | 25.7% |
| Others | 7.4% |

EXAMPLE 29

0.4 Part of silicotungstic acid (water content, 5%) recovered in Example 18 and 100 parts of p-cresol were added to a flask, and water was added so that the water content of the mass in the flask was 0.004 time by weight based on p-cresol. Thereafter, 242 parts of an LBB gas (isobutene content, 45%) was bubbled into the mass over 7 hours with stirring while maintaining the temperature at from 50° to 55° C.

After completion of the reaction, the precipitated silicotungstic acid was filtered off at a temperature of 50° C. by means of a glass filter (G4). The weight of the recovered silicotungstic acid was 0.38 part. The filtrate was washed with a small amount each of water and aqueous alkali to obtain 195.2 parts of an oily product.

The composition of this oily product was analyzed by gas chromatography to obtain the following result:

| | |
|---|---|
| Unreacted p-cresol | 0.9% |
| 2-Tert-butyl-4-methylphenol | 10.5% |
| 2,6-Di-tert-butyl-4-methylphenol | 84.5% |
| Others | 4.1% |

The content of isobutene dimer and isobutene trimer of the unreacted gas was 0.5%.

EXAMPLE 30

100 Parts of a cresol mixture (p-cresol, 70%; m-cresol, 30%) and 0.8 part of silicotungstic acid was added to a flask, and reaction was carried out in the same manner as in Example 28.

After completion of the reaction, the reaction solution was centrifuged on a centrifuge (centrifugal effect, 2000G) to separate the mixture into an oily layer which is a supernatant and the layer of precipitated silicotungstic acid. The content of silicotungstic acid of the oily layer, a supernatant, was 0.01 wt. %.

The weight of the precipitated silicotungstic acid layer was 3 parts. This layer and 100 parts of a cresol mixture (p-cresol, 70%; m-cresol, 30%) were added to a flask, and water was added so that the water content of the mass in the flask was 0.02 time by weight based on the cresol mixture.

Thereafter, 288 parts of an LBB gas (isobutene content, 45%) was bubbled into the mass over 5 hours with stirring while maintaining the temperature at from 50° to 55° C.

The weight of the reaction mixture was 204.1 part.

After removing the precipitated silcotungstic acid from the reaction mixture, washing with water and aqueous alkali was carried out to obtain 190.1 parts of an oily product. The composition of this oily product was analyzed by gas chromatography to obtain the following result:

| | |
|---|---|
| Unreacted cresol | 0.5% |
| 2-Tert-butyl-4-methylphenol | 18.0% |
| 6-Tert-butyl-3-methylphenol | 3.3% |
| 2,6-Di-tert-butyl-4-methylphenol | 48.0% |
| 4,6-Di-tert-butyl-3-methylphenol | 26.2% |
| Others | 4.0% |

The content of isobutene dimer and isobutene trimer of the unreacted gas was 0.4%.

EXAMPLE 31

100 Parts of a cresol mixture (p-cresol, 70%; m-cresol, 30%) and 1 part of silicotungstic acid were added to a flask, and 288 parts of an LBB gas (isobutene content, 45%) was bubbled into the mixture over 5 hours with stirring while maintaining the temperature at from 45° to 55° C. The weight of the resulting reaction mixture was 190.9 parts. Separately from this, 30 parts each of water was added to the mixer and settler of vertical-type mixer/settler two-stage assembly, and the above reaction mixture was continuously supplied to the assembly at a rate of 150 parts/hour over 12.5 hours to recover the silicotungstic acid catalyst into the aqueous layer. The silicotungstic acid concentration of the aqueous layer in the first stage was 24.0%, and the weight of the layer was 39.5 parts. The same concentration of the aqueous layer in the second stage was 0.65%, and the weight of the layer was 30.2 parts (total percent recovery of silicotungstic acid, 98.5%).

Additional water was continuously supplied to the first stage because water in the assembly decreased in solution in the reaction mixture. The oily layer was washed with a small amount of aqueous alkali, and its composition was analyzed by gas chromatography to obtain the following result:

| | |
|---|---|
| Unreacted cresol | 0.6% |
| 2-Tert-butyl-4-methylphenol | 17.2% |
| 6-Tert-butyl-3-methylphenol | 3.2% |
| 2,6-Di-tert-butyl-4-methylphenol | 47.3% |
| 4,6-Di-tert-butyl-3-methylphenol | 25.6% |
| Others | 6.6% |

EXAMPLE 32

4.2 Parts of the aqueous silicotungstic acid solution recovered in Example 31 and 100 parts of a cresol mixture (p-cresol, 70%, m-cresol, 30%) were added to a flask.

Reaction was carried out in the same manner as in Example 31 to obtain 190.8 parts of a reaction mixture. The silicotungstic acid catalyst was extraction-recovered with water in the same manner as in Example 31 except that the aqueous layer in the second stage in Example 31 was used as water to be added to the first stage. The silicotungstic acid concentration of the aqueous layer in the first stage was 24.5%, and the weight of the layer was 39.2 parts. The same concentration of the aqueous layer in the second stage was 0.70%, and the weight of the layer was 30.1 parts (total percent recovery of silicotungstic acid 97.2%).

The oily layer was treated in the same manner as in Example 31 and analyzed for the composition by gas chromatography to obtain the following result. By repeating the procedures of Examples 31 and 32, the expensive silicotungstic acid catalyst can be recovered and reused.

| | |
|---|---|
| Unreacted cresol | 1.0% |
| 2-Tert-butyl-4-methylphenol | 15.6% |
| 6-Tert-butyl-3-methylphenol | 2.0% |
| 2,6-Di-tert-butyl-4-methylphenol | 49.8% |
| 4,6-Di-tert-butyl-3-methylphenol | 27.2% |
| Others | 3.8% |

EXAMPLE 33

Two parts of the aqueous silicotungstic acid solution recovered in Example 31 and 100 parts of m-cresol were added to a flask.

Thereafter, 109.5 parts of an isobutene gas was bubbled into the mixture over 10 hours with stirring while maintaining the temperature at from 50° to 55° C. After completion of the reaction, 1.5 parts of water was added to dissolve the precipitated silicotungstic acid in water, and the reaction mixture was separated into two layers to obtain 1.93 parts of an aqueous solution containing 23.9% of silicotungstic acid (total percent recovery of silicotungstic acid, 96.1%).

The oily layer was washed with a small amount of aqueous alkali to obtain 198.7 parts of an oily product. The composition of this oily product was analyzed by gas chromatography to obtain the following result:

| | |
|---|---|
| Unreacted m-cresol | 0.9% |
| 6-Tert-butyl-3-methylphenol | 8.4% |
| 4,6-Di-tert-butyl-3-methylphenol | 86.7% |
| Others | 4.1% |

Further, reaction was repeated in the above except that 2 parts of the 23.9 % aqueous silicotungstic acid solution recovered above and 100 parts of m-cresol were added to the flask. The silicotungstic acid catalyst was extraction-recovered with water, and the oily layer was washed with aqueous alkali to obtain 198.5 parts of an oily product.

The composition of this oily product was analyzed by gas chromatography to obtain the following result:

| | |
|---|---|
| Unreacted m-cresol | 1.1% |
| 6-Tert-butyl-3-methylphenol | 8.7% |
| 4,6-Di-tert-butyl-3-methylphenol | 86.3% |
| Others | 3.8% |

Thus, 1.92 parts of a 23.7% aqueous silicotungstic acid solution was obtained (total percent recovery of silicotungstic acid 95.2%).

By repeating the procedure of this example, the expensive silicotungstic acid catalyst can be recovered and re-used.

EXAMPLE 34

100 Parts of p-cresol and 0.4 part of phosphotungstic acid were added to a flask, and reaction was carried out by bubbling 288 parts of an LBB gas (isobutene content, 45%) into the mixture over 5 hours with stirring while maintaining the temperature at from 50° to 55° C.

The weight of the reaction product after completion of the bubbling was 207.6 parts. This reaction product was washed with two 100-part portions of 80° C. warm water to separate 194.1 parts of an oily layer.

Analysis of the composition of this oly layer by gas chromatography showed that the content of 2,6-di-tert-butyl-4-methylphenol was 77.7%.

This oily layer was rectified under reduced pressure to obtain 146.3 parts of a fraction having a boiling point of 142°-147° C./20 torr (corresponding to 2,6-di-tert-butyl-4-methylphenol). The yield was 71.8%.

The yield of the desired product further more increases by re-reacting, 2-tert-butyl-4-methylphenol obtained as a forerun (120°-135° C./20 torr).

EXAMPLE 35

100 Parts of a cresol mixture (p-cresol, 70%; m-cresol, 30%) and 0.15 part of silicotungstic acid were added to a flask, and reaction was carried out by bubbling 288 parts of an LBB gas (isobutene content, 45%) into the mixture over 10 hours with stirring while maintaining the temperature at from 45° to 55° C.

The weight of the reaction product after completion of the bubbling was 210.3 parts. This reaction product was neutralized by washing with 60 parts of a 3% aqueous sodium hydroxide solution (60° C.), and then washed with 60 parts of 60° C. warm water to separate 192.5 parts of a oily layer. The composition of this oily layer was analyzed by gas chromatography to obtain the following result:

| | |
|---|---|
| 2-Tert-butyl-4-methylphenol | 15.1% |
| 6-Tert-butyl-3-methylphenol | 4.7% |
| 2,6-Di-tert-butyl-4-methylphenol | 52.5% |
| 4,6-Di-tert-butyl-3-methylphenol | 24.1% |

This oily layer was rectified under reduced pressure to obtain firstly 99.0 parts of 2,6-di-tert-butyl-4-methylphenol and subsequently 48.6 parts of 4,6-di-tert-butyl-3-methylphenol (165°-168° C./20 torr).

The yield of 2,6-di-tert-butyl-4methylphenol was 69.4% based on p-cresol.

The yield further more increases by re-reacting 2-tert-butyl-4-methylphenol and 6-tert-butyl-3-methylphenol obtained as a forerun (118°-135° C./20 torr).

EXAMPLE 36

10 Parts of p-cresol and 0.05 part of phosphomolybdic acid were added to a flask, and reaction was carried out by bubbling 288 parts of an LBB gas (isobutene content, 45%) into the mixture over 7 hours with stirring while maintaining the temperature at from 70° to 75° C.

The weight of the reaction product after completion of the bubbling was 203.1 parts.

This reaction product was washed with two 100-part portions of 60° C. warm water (contact time, 20 minutes) to separate 190.6 parts of an oily layer.

The composition of this oily layer was analyzed by gas chromatography to obtain the following result:

| | |
|---|---|
| 2,6-Di-tert-butyl-4-methylphenol | 74.4% |
| 2-Tert-butyl-4-methylphenol | 21.2% |
| p-Cresol | 1.0% |
| Others | 3.5% |

The oily layer was rectified under reduced pressure on a distillation tower having 25 theoretical plates to obtain 140.2 parts of a fraction having a boiling point of 145°-147° C./20 torr (corresponding to 2,6-di-tert-butyl-4-methylphenol). The yield was 68.8%.

COMPARATIVE EXAMPLE 1

100 Parts of a cresol mixture (p-cresol, 70%; m-cresol, 30%) and 2.0 parts of conc. sulfuric acid were added to a flask, and 288 parts of an LBB gas (isobutene content, 45%) was bubbled into the mixture over 8 hours with stirring while maintaining the temperature at from 60° to 65° C.

The weight of the reaction mixture was 208.3 parts.

The reaction product was washed with water and aqueous alkali to obtain 191.0 parts of an oily product. The composition of this oily product was analyzed by gas chromatography to obtain the following result:

| | |
|---|---|
| Unreacted cresol | 1.3% |
| 2-Tert-butyl-4-methylphenol | 8.5% |
| 6-Tert-butyl-3-methylphenol | 9.3% |
| 2,6-Di-tert-butyl-4-methylphenol | 54.0% |
| 4,6-Di-tert-butyl-3-methylphenol | 15.0% |
| Others | 11.9% |

The content of isobutene dimer and isobutene trimer of the unreacted gas was 5.9%.

COMPARATIVE EXAMPLE 2

100 Parts of p-cresol and 3.0 parts of conc. sulfuric acid were added to a flask, and 110 parts of an isobutene gas was bubbled into the mixture over 5 hours with stirring while maintaining the temperature at from 55° to 65° C.

The weight of the reaction mixture was 207.0 parts.

This reaction product was washed with water and aqueous alkali to obtain 198.8 parts of an oily product. The composition of this oily product was analyzed by gas chromatography to obtain the following result:

| | |
|---|---|
| Unreacted p-cresol | 1.5% |
| 2-Tert-butyl-4-methylphenol | 6.0% |
| 2,6-Di-tert-butyl-4-methylphenol | 79.7% |
| Others | 12.8% |

The content of isobutene dimer and isobutene trimer of the unreacted gas was 5.6%.

COMPARATIVE EXAMPLE 3

208.3 Parts of the reaction product obtained in Comparative example 1 was neutralized by washing with 200 parts of a 20% aqueous sodium hydroxide solution (80° C.) (contact time, 60 minutes), and then washed with 100 parts of 80° C. war water to separate 187.0 parts of an oily layer. The composition of this oily layer was analyzed by gas chromatography to obtain the following result:

| | |
|---|---|
| 2,6-Di-tert-butyl-4-methylphenol | 55.9% |
| 4,6-Di-tert-butyl-3-methylphenol | 15.8% |
| 2-Tert-butyl-4-methylphenol | 8.5% |
| 6-Tert-butyl-3-methylphenol | 9.3% |
| Unreacted cresol | 0.3% |
| Others | 10.2% |

The oily layer was rectified under a reduced pressure of 20 torr. When the temperature in the still reached about 90° C., debutylation occurred and evolution of an isobutyelene, gas began. The weight of desired 2,6-di-tert-butyl-4-methylphenol was 10.2 parts and the yield thereof was 7.2% based on p-cresol.

COMPARATIVE EXAMPLE 4

100 Parts of p-cresol and 5.0 parts of p-toleunesulfonic acid were added to a flask, and reaction was carried out by bubbling 288 parts of an LBB gas (isobutene content, 45%) into the mixture over 10 hours with stirring while maintaining the temperature at from 70° to 75° C.

The weight of the reaction product after completion of the bubbling was 205.1 parts.

This reaction product was neutralized by washing with 200 parts of a 20% aqueous sodium hydroxide solution (80°0 C.) (contact time, 60 minutes), and then washed with 100 parts of 80° C. warm water to separate 188.7 parts of an oil layer. Analysis of the composition of this oily layer by gas chromatography showed that the layer contained 7.51% of 2,6-di-tert-butyl-4-methylphenol. This oily layer was rectified under reduced pressure in the same manner as in Comparative example 3. When the temperature in the still reached about 90° C., evolution of an isobutylene gas began. The weight of desired 2,6-di-tert-butyl-4-methylphenol was 13.5 parts, and the yield thereof was 6.6%.

What we claim is:

1. A process for producing a hydroxy-containing alkylated aromatic compound, which comprises reacting, in liquid phase and at a temperature of 30°-150° C., an aromatic compound having at least one hydroxyl group selected from the group consisting of monohydric phenols, polyhydric phenols and naphthols, with an alkylating agent selected from the group consisting of *isobutene,* compounds represented by the formula:

$$R_1—CH=CH_2$$

wherein $R_1$ represents a straight or branched hydrocarbon residue having 1-10 carbon atoms, compounds represented by the formula:

$$R_2CH=CH—CH_3$$

wherein $R_2$ represents a straight or branched hydrocarbon residue having 1-9 carbon atoms, and cyclic unsaturated hydrocarbon shaving up to 10 carbon atoms, wherein the alkylating agent is used in an amount of 0.1-30 moles per mole of the aromatic compound, and the reaction is conducted in the presence of a heteropoly acid in an amount of [0.000-0.3] *0.00001-0.3* times by weight, and in the presence of water in an amount of 0.001-0.10 times by weight, based on the weight of the aromatic compound.

2. A process according to claim 1 wherein the heteropoly acid is at least one member selected from the group consisting of phosphomolybdic acid, silicomolybdic acid, arsenomolybdic acid, telluromolybdic acid, aluminomolybdic acid, silicotungstic acid, phosphotungstic acid, borotungstic acid, titanotungstic acid and stannotungstic acid.

3. A process according to claim 1 wherein the aromatic compound is o-cresol, m-cresol, p-cresol or a cresol mixture containing p-cresol.

4. A process according to claim 3 wherein the aromatic compound is p-cresol or a cresol mixture containing p-cresol.

5. A process according to claim 1 wherein the alkylating agent is isobutene or isobutene-containing gas.

6. A process according to any one of claims 1, 3, 4, and 5 wherein the heteropoly acid is silicotungstic acid.

7. A process according to claim 1 wherein the amount of water is 0.001-0.05 times the weight of the aromatic compound.

8. A process according to any one of claims 1, 2, 3, 4, 5 and 7 wherein the heteropoly acid is separated, after the reaction, for re-use.

9. A process according to claim 8 wherein the separation of the heteropoly acid is conducted by treating the reaction mixture with water to obtain an aqueous layer containing the heteropoly acid.

10. A process according to claim 8 wherein the separation of the heteropoly acid is conducted by precipitating the heteropoly in the reaction system.

11. A process according to claim 9 wherein the content of the heteropoly acid in the aqueous layer is not less than 20% by weight.

12. A process according to claim 1 wherein the temperature at which the aromatic compound is reacted with the alkylating agent is a temperature of 40°-90° C.

* * * * *